(12) United States Patent
Starks

(10) Patent No.: US 9,702,868 B1
(45) Date of Patent: Jul. 11, 2017

(54) METHOD OF MEASURING POLYPHENOL ANTIOXIDANTS IN SORGHUM AND OTHER PLANT MATTER AND METHOD OF SELECTION OF SPECIFIC SORGHUM VARIETIES FOR EXTRUSION PURPOSES

(71) Applicant: Milo Insulation, LLC, Fort Worth, TX (US)

(72) Inventor: Aubrie N. Starks, Haltom City, TX (US)

(73) Assignee: Milo Insulation, LLC, Ft. Worth, TX (US)

( * ) Notice: Subject to any disclaimer, the term of this patent is extended or adjusted under 35 U.S.C. 154(b) by 258 days.

(21) Appl. No.: 14/288,583

(22) Filed: May 28, 2014

(51) Int. Cl.
  *A23L 1/00* (2006.01)
  *A01H 5/00* (2006.01)
  *G01N 33/50* (2006.01)

(52) U.S. Cl.
  CPC .............................. *G01N 33/5097* (2013.01)

(58) Field of Classification Search
  CPC .................................. A23L 1/00; A01H 5/00
  USPC ........ 436/161; 426/448, 449, 450, 469, 478, 426/516; 800/320
  See application file for complete search history.

(56) References Cited

U.S. PATENT DOCUMENTS

| | | | |
|---|---|---|---|
| 2,759,956 | A | 8/1956 | Pominski et al. |
| 3,481,960 | A | 11/1967 | Kinsey et al. |
| 4,313,880 | A | 2/1982 | Redaelli |
| 5,705,618 | A | 1/1998 | Westcott et al. |
| 5,713,526 | A | 2/1998 | Martin et al. |
| 5,820,039 | A | 10/1998 | Martin et al. |
| 6,312,753 | B1 | 11/2001 | Kealey et al. |
| 6,894,136 | B2 | 5/2005 | Markham et al. |
| 6,939,937 | B2 | 9/2005 | Markham et al. |
| 6,965,005 | B2 | 11/2005 | Markham et al. |
| 8,541,045 | B2 | 9/2013 | Kealey et al. |
| 2005/0160662 | A1 | 7/2005 | Jordan |
| 2007/0014912 | A1 | 1/2007 | Mazza et al. |
| 2007/0141178 | A1 | 6/2007 | Empie et al. |
| 2014/0228429 | A1* | 8/2014 | Funda et al. ............... 514/458 |
| 2015/0056345 | A1* | 2/2015 | Elemans et al. ............ 426/250 |
| 2015/0297522 | A1* | 10/2015 | Teleki ........................ 426/250 |
| 2015/0320683 | A1* | 11/2015 | Teleki ........................ 426/250 |

OTHER PUBLICATIONS

Cooperative Extension Service, University of Arkansas, Grain Sorghum Production Handbook, 2004, pp. 1-75, MP297-3M-1-04RV.
Agbangnan D., P.C., et al., Optimization of the Extraction of Sorghum's Polyphemols for Industrial Production by Membrane Processes, 2012, Research Journal of Recent Sciences, vol. 1 (4), pp. 1-8.
Anwar, F., et al., Effect of Solvents Extraction on Total Phenolics and Antioxidant Activity of Extracts from Flaxseed, 2012, Acta Sci. Pol., Technol Aliment, vol. 11 (3), pp. 293-301.
Awika, J.M., et al., Sorghum Phytochemicals and Their Potential Impact on Human Health, 2004, Phytochemistry, vol. 65, pp. 1199-1221.
Awika, J. M., et al., Screenng Methods to Measure Antioxidant Activity of Sorghum and Sorghum Products, 2003, J. Agric. Food Chem., vol. 51, pp. 6657-6662.
Barros, F., et al., Accelerated Solvent Extraction of Phenolic Compounds from Sorghum Brans, 2013, Journal of Cereal Science, vol. 58, pp. 305-312.
Chavan, J.K., et al., Removal of Tannins and Improvement of in Vitro Protein Digestibility of Sorghum Seeds by Soaking in Slkali, 1979, Journal of Food Science, vol. 44, pp. 1319-1321.
Dalton, J.S., et al., Fractionation of Sorghum Grain Wax, 1959, Agricultural and Food Chemistry, vol. 7, No. 8, pp. 570-573.
Kim J., Wax Extraction and Characterization from Full-Fat and Defatted Rice Bran, 2008, Dissertation to Graduate Faculty of Louisiana State University, pp. i-122.
Polycarpe Kayode, A.P., et al., Uncommonly High Levels of 3-Deoxyanthocyanidins and Antioxidant Capacity in the Leaf Sheaths of Dye Sorghum, 2011, J. Agric. Food. Chem, vol. 59, pp. 1178-1184.

* cited by examiner

*Primary Examiner* — Brian J Sines
(74) *Attorney, Agent, or Firm* — Grady K. Bergen; Griggs Bergen LLP

(57) ABSTRACT

A method of determining relative polyphenol antioxidant levels in plant matter, particularly whole sorghum seeds, is carried out by combining a selected amount of solid plant matter to be evaluated with a solvent and a polyphenol extraction agent to form a stirrable mixture. The mixture is heated to approximately the boiling point of the solvent with agitation of the mixture for a period of at least 1½ hours. The heated mixture is filtered while the liquid is at a temperature of not more than 5° C. below the boiling point of the solvent to obtain an extractant solution filtrate. From this filtrate, a concentrated extractant solution is formed, cooled, and filtered to form a final filtrate. An analytical sample of this final filtrate is then introduced into a high performance liquid chromatography (HPLC) system to separate and determine the relative amounts of polyphenol antioxidants in the plant matter. This technique can be used in determining polyphenol antioxidant levels in varieties of whole sorghum seeds to select specific varieties that are most appropriate for extrusion applications.

9 Claims, No Drawings

METHOD OF MEASURING POLYPHENOL ANTIOXIDANTS IN SORGHUM AND OTHER PLANT MATTER AND METHOD OF SELECTION OF SPECIFIC SORGHUM VARIETIES FOR EXTRUSION PURPOSES

BACKGROUND

Sorghum is a domesticated plant well known to man. It has been hybridized since early Egyptian times and is highly diversified in its varieties. As used herein, the terms "sorghum" and "milo" may be used interchangeably. In the United States, varieties of sorghum have few uses other than for animal feed or as a less expensive feed grain substitute for corn or wheat. In other parts of the world, particularly Africa and Asia, sorghum is used for flour and human food.

There are hundreds of varieties of sorghum with each variety having slightly different characteristics. One area in which sorghum varieties differ from one another is in their antioxidant content. Sorghum typically contains the antioxidant chemical compounds classified as tocopherols, anthocyanins, and polyphenols. Each variety of sorghum may contain a specific combination of one or more of these antioxidants in different amounts within the various components or structures of the plant. Thus, for example, the seed hull of a specific sorghum variety may contain different antioxidants at amounts that are different from those in the endogerm of the same seed.

In certain applications, sorghum may be extruded into a matrix for various purposes. In one such application, the extruded matrix may be used as a construction component, such as an insulation material. Not all sorghum is created equal for extrusion purposes, however. Some varieties may extrude very well, while others may not extrude at all or only with great difficulty, depending on the desired characteristics of the final extruded product. Heretofore, to determine whether a particular variety of sorghum would yield an extrusion product having desirable characteristics, it was necessary to test the sorghum in an actual extrusion process. This is time consuming and inefficient, however, and requires utilization of expensive extrusion equipment that could otherwise be used in more productive applications.

DETAILED DESCRIPTION

The present invention provides a method of evaluating plant matter and determining the relative amounts of antioxidants of such plant matter. In particular, the plant matter is evaluated using specific analysis techniques to determine the relative polyphenol antioxidant levels of the plant matter. While the method may be used for any plant matter containing polyphenol antioxidants, the method has particular application for and is useful in determining the relative levels of polyphenols in sorghum. Moreover, the method has application for and is useful in determining relative polyphenol levels in whole sorghum seeds, berries or grains, without removing the hull of the sorghum seed. As used herein, the expressions "seeds," "berries," or "grains" are meant to refer to the same thing and may be used interchangeably.

With respect to determining the relative polyphenol levels in whole sorghum seeds, this is particularly useful when considering the sorghum for use in extrusion applications. It has been discovered that when analysis techniques carried out in accordance with the method of the invention are used in determining relative polyphenol levels in whole sorghum seeds, those whole seeds having a certain relative polyphenol level produce desired extrusion characteristics that are not produced by sorghum seeds that have lower relative polyphenol levels. The use of the expression "relative polyphenol levels" or similar expressions is meant to address the fact that different polyphenol levels may be determined based upon the physical state of the material tested. By way of example, whole sorghum seeds tested for polyphenols will typically have a lower detected level compared to the same seeds tested after they have been ground. This is because polyphenols are extracted from the surfaces of the test material, and a ground seed has more exposed surface area than a whole seed. Thus, the polyphenol level detected for whole seeds of a particular sorghum variety is a relative amount, since the nature of the test material is defined as "whole seed".

The following description of analysis techniques is directed to testing and evaluating whole sorghum seeds for relative polyphenol levels. It should be understood, however, that the analysis techniques may be applied for determining relative levels of other antioxidants in other plant matter, including non-seed plant components and non-sorghum plants. This includes non-whole seeds or such components that have been broken, ground, chopped, crushed, pulverized, milled, or otherwise formed into non-whole particles or other non-whole forms, whether they be derived from seeds, grains, or other plant matter components. Such analysis may be used for plant matter from a single variety of plant or from a mixture of different varieties.

With respect to analyzing whole sorghum seeds, the analysis may be conducted with a quantity or amount of seeds from a single sorghum variety. As used herein, the expression "single variety" refers to plant material from a single taxonomic variety or cultivar. Such seeds or other plant matter are those that contain the same inheritable or reproducible characteristics.

The whole sorghum seeds are those non-broken seeds with the outer hull still being substantially intact and with the germ and endogerm still being substantially contained within the outer hull layers. Generally, whole seeds of a single variety of sorghum will be of similar sizes. Thus, non-whole or partial seed fragments may be easily separated and removed from whole seeds by sieving or common particle separation methods. It should be noted that such whole sorghum seeds may include seeds that have some small cracks or fissures in the outer hull but that otherwise appear as whole seeds through unaided visual inspection. As used herein, the expressions "whole sorghum seeds", "whole milo seeds", or similar expressions is also meant to encompass a limited amount of non-whole seeds and other non-seed matter, such as leaf or stem fragments, that may not be separated from the whole seeds. Such an amount of non-whole or broken seeds may exist due to breakage occurring before or during the method or from inefficient particle separation methods. Such amounts of non-whole seeds or non-seed matter may comprise 1% or less of the total amount of seeds being analyzed.

In the analysis technique, the seeds are combined with a solvent and a polyphenol extraction agent. The solvent is typically an alcohol. Low molecular weight alcohols such as methanol and ethanol are particularly useful as solvents. In general applications, methanol is used as the solvent due to its low boiling point and ease of distillation.

The amount of methanol or other solvent used should be sufficient to provide a stirrable mixture when combined with the plant matter. For whole sorghum seeds, an amount of 3 to 5 mL of solvent per gram of whole sorghum seeds is recommended. This amount of solvent has been found to be effective in providing a stirrable mixture, wherein the seeds may be generally maintained in a suspension with agitation and to prevent excessive dilution of the extracted polyphenols. For non-whole seeds or other non-seed plant matter, different amounts of solvent may be needed to provide a stirrable mixture and to prevent excessive polyphenol dilution.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

The polyphenol extraction agent is typically a hydroxide-containing compound. Various hydroxide-containing basic (i.e., pH >7) compounds may be used. In particular, potassium hydroxide (KOH) and sodium hydroxide (NaOH) have been found to be highly suitable extraction agents for the polyphenols. Potassium hydroxide and sodium hydroxide are particular useful because they are both strong bases and readily dissolve in the alcohol solvent. The amount of KOH or NaOH polyphenol extraction agent used with the whole sorghum seeds is selected to insure quantitative extraction of polyphenols from the whole seeds. This may be from 0.01 gram or more of extraction agent per gram of whole sorghum seeds. In particular embodiments, from 0.01 gram to 0.04 gram of extraction agent per gram of whole sorghum seeds may be used, more particularly from 0.01 gram to 0.03 gram of extraction agent per gram of whole sorghum seeds, with 0.02 gram of extraction agent per gram of whole sorghum seeds being particularly useful. While higher amounts of extraction agent may be used, it has been shown that this does not lead to higher levels of polyphenol being extracted.

The sorghum seeds, solvent, and extraction agent are combined in an appropriate vessel, and the mixture is heated to facilitate extraction of polyphenols. The heating is carried out while agitating the mixture within the vessel to maintain the sorghum seeds in a substantially suspended state within the solvent so that they do not readily settle out. The agitation is typically carried out through the use of a suitable stirring mechanism(s), although other agitation means may be used.

The heating may be carried out at temperatures of from 50° C. to 100° C. Typically, the heating temperature may be limited to the boiling temperature of the particular solvent or solvent mixture used. Thus, for methanol, the boiling point is about 64.7° C. For ethanol, the boiling point is about 78.4° C. Solvent vapors that evolve from the mixture during heating may be condensed and recycled back to the mixture. A reflux condenser or similar apparatus may be used for this purpose.

Heating, which may be at the boiling point of the solution, is carried out for an amount of time sufficient to ensure that the polyphenols are quantitatively extracted from the seeds. Seeds of different varieties of sorghum have polyphenols that are released into solution at different rates. Heating for less than 1½ hours may produce proportionately lower levels of polyphenols being extracted from the various varieties; heating for periods longer than 2 hours has been shown not to increase the levels of polyphenol extracted from the various varieties, however. Thus, the heating may be carried out for a period of at least 1½ hours or 2 hours to account for these different rates of extraction in certain applications.

After heating, the mixture is immediately filtered to remove any solids from the mixture. The solids constitute the seeds, with any other solid matter, such as minor amounts of any leaf, steam fragments, etc., that might be included in the mixture. The filter media may be a rapid qualitative paper filter. An example of suitable filter media may be that commercially available as Whatman® Grade 1 filter paper (11 μm) or its equivalent. One or more filter media may be used during the filtering process. Filtering of the hot test sample mixture is done to eliminate or minimize any solidification and/or aggregation of fats, oils, waxes, or other materials in the heated liquid that could solidify at cooler temperatures and be filtered out, thus entrapping solvent and dissolved polyphenols. Thus, filtration techniques should be used so that there is minimal temperature drop of the liquid to avoid solidification of fats, oils, and waxes. Filtering the mixture using filtering techniques so that there is a liquid temperature drop of 5° C. or less through the duration of the filtering step may be suitable. Such filtration techniques may include vacuum or suction filtration techniques that result in more rapid filtration.

After filtration, the liquid filtrate is collected, and the solvent is evaporated off to concentrate the seed extractant solution. Various methods may be used to achieve this, such as common distillation techniques wherein the solution is heated to the boiling point of the solvent to distill off the solvent. The evaporated solvent may be collected for reuse, if desired. The amount of solvent evaporated to form the concentrated extractant solution may vary. In practice, evaporation of solvent to provide a final concentrated solution that is about ⅓ to ⅕ of the initial volume of the collected filtrate has been found to be suitable. It may be desirable to evaporate a quantity of solvent from the filtrate to the point where the concentrate remains readily pourable after chilling or cooling, as is described later on, but where it does not become too thick so that it becomes slow to pour or where it begins to have the consistency of syrup.

After the extractant is concentrated, it is cooled or chilled. This may be done in an ice bath or at a reduced temperature. The concentrated extractant solution may even be allowed to sit overnight or for a sufficient length of time at room temperature (approx. 20° C.) or below. This cooling or chilling ensures that any fats, oils, waxes or other materials are allowed to solidify and/or aggregate so that they may be filtered out of the cooled extractant solution.

The cooled concentrated extractant solution is filtered to remove solidified and/or aggregated materials contained within the concentrated extractant solution. This may be accomplished using glass fiber filter media, such as a GF/A grade glass media (1.6 μm) or equivalent. One or more filter media may be used during the filtering process. In certain applications, the use of double GF/A glass filters has been found to be useful. Filtration of the cooled concentrated extractant solution may be carried out under vacuum. The filtered solids may be collected and discarded.

The concentrated extractant solution filtrate is collected and may be used for a liquid sample for chemical analysis wherein polyphenol components may be separated, detected, and quantitatively measured. Before use in liquid chromatography analysis, the concentrated extractant solution filtrate may be further diluted with additional solvent. The solvent added may provide from 0.8 mL to 1.2 mL of final extractant solution per gram of whole milo seed initially used in the extraction procedure. In certain embodiments, a standard concentration is prepared by the addition of solvent to provide an equivalent to 1.0 mL of final extractant solution per gram of whole sorghum seed initially used in the extraction procedure. This level of dilution has been found to be useful in comparing polyphenol levels for whole sorghum seeds when using high-performance liquid chromatography (HPLC) analysis techniques. Thus, for example, if 100 grams of sorghum seeds were used in the extraction of the polyphenols, the concentrated extractant solution is diluted to a final solution volume of 100 mL. If 50 grams of sorghum seeds were used in the extraction procedure, the final extractant solution may be diluted to a final volume of 50 mL. This, in essence, provides a final extractant solution that contains the polyphenols from 1 gram of sorghum seeds per mL of solution, which may be used for computation and comparison of sorghum seed varieties.

In testing for polyphenol levels, liquid chromatography analysis techniques are used. This is typically done through HPLC analysis utilizing a C-18 reverse-phase analytical column. HPLC systems are commonly used in various chemical analyses and are thus well known by those skilled in the art. In the analysis of polyphenols levels from plant matter, particular in the case of whole sorghum seeds, a mobile phase that is capable of providing a very sharp signal for polyphenols is preferred. Acetonitrile was found to be particularly useful as an organic component of the mobile phase system for detecting polyphenols. This is combined with an aqueous component, which may contain an acid at a concentration of $0.05\%_{v/v}$ to $0.15\%_{v/v}$ relative to the aqueous portion. The mobile phase may be an acetonitrile/ aqueous mixture that is comprised of from $40\%_{v/v}$ to $95\%_{v/v}$ acetonitrile, with the balance being the aqueous component. In particular embodiments, the mobile phase for the HPLC analysis may be comprised of acetonitrile and an aqueous phosphoric acid ($H_3PO_4$) solution. The aqueous phosphoric acid solution may have a phosphoric acid concentration of from $0.05\%_{v/v}$ to $0.15\%_{v/v}$, with $0.1\%_{v/v}$ being shown to be particularly useful. In certain embodiments, the amount of acetonitrile in the mobile phase may range from $85\%_{v/v}$ to $95\%_{v/v}$ with the aqueous phosphoric acid solution making up the balance (i.e., from $5\%_{v/v}$ to $15\%_{v/v}$). And in particular embodiments, a mobile phase consisting of $90\%_{v/v}$ acetonitrile and $10\%_{v/v}$ of an aqueous phosphoric acid solution at $0.1\%_{v/v}$ phosphoric acid has been found useful in the testing of polyphenol levels in whole sorghum seeds. In operating the HPLC, the mobile phase may be delivered at a flow rate of from 1 to 3 mL/min.

The HPLC system may utilize a UV/visible wavelength detector with a detection wavelength range from 210 nm to 640 nm. In particular embodiments, the detection wavelength may be set at from 315 to 335, more particularly from 320 nm to 325 nm, for detecting polyphenols when utilizing an apigenin/luteolin polyphenol standard. In practice, a detection wavelength of approximately 323 nm has been found to be particularly useful in testing for polyphenol levels. This particular wavelength has been found to be the maximum absorption wavelength for apigenin/luteolin.

A high-resolution analytical HPLC column size is typically 250 mm×4.6 mm, although other sizes may be used. A reverse-phase column is typically packed with silica particles having an average particle size of about 5 μm. For optimum separation analyses, the binding site or stationary phase component of the column may be an octadecyl carbon chain polymer, commonly called "C-18", bound to the silica support material.

When measuring final extractant solutions for polyphenol levels, a comparison standard having a known polyphenol concentration is used. This standard is run through the HPLC system to ensure that the HPLC components are functioning properly and to establish retention times and signal areas. Replicate runs may be used for the standard and each extractant sample. A suitable standard material may be pure apigenin or pure luteolin (e.g., approx. 99+% pure) or a mixture of these (e.g., 100 parts apigenin/50 parts luteolin). Apigenin and luteolin are both well-known polyphenol antioxidants and their detection in known concentrations by HPLC provides a reference for determining the polyphenol levels in test extractant solutions. Other polyphenol antioxidant compounds may also be used. The standard material is dissolved at a known concentration (e.g., 150 ppm) in the same solvent used for the extractant and is used for comparison with the extractant samples. Using the known concentration of the polyphenol standard and the relative HPLC signals of the standard and extractant, the concentration of polyphenols in the whole sorghum seed extractant sample can then be directly calculated.

From these analysis techniques used in determining polyphenol levels extracted from whole sorghum seeds, a sorghum variety can be selected for use as a sorghum extrusion stock material that provides good extrusion characteristics and good final extruded product. Specific selected varieties of sorghum seeds that have been evaluated using the whole seed extraction and analysis techniques, as has been previously described, which exhibit a polyphenol content of from 100 ppm, 110 ppm, 120 ppm, 130 ppm, 140 ppm, and 150 ppm or more polyphenols by weight of the sorghum seeds evaluated have been found to be particularly useful for extrusion applications. Such varieties produce homogeneous stock materials that extrude smoothly and continuously without plugging of extruder equipment and yield products which are consistently uniform and have low densities within a narrow density range.

After evaluating samples of whole seeds for polyphenol level, a specific variety of sorghum that exhibits a high level of polyphenols (e.g., >150 ppm) may be selected for use as an extrusion stock material. Typically, only a single variety of sorghum is used in the extrusion operation, as mixtures of different varieties of sorghum have been found to negatively impact the extrusion operation, providing inconsistent extrusion and variations in the extruded product. Thus, a suitable selected extrusion stock material is a specific sorghum variety the seeds of which exhibit a polyphenol content of from 100 ppm, 110 ppm, 120 ppm, 130 ppm, 140 ppm, and 150 ppm or more.

The single variety of whole sorghum seeds used for the selected extrusion stock material is first sized and cleaned. The seeds are run through a clipper mill or similar equipment to remove small and/or broken seeds. The whole, uniform-sized seeds are then run through a destoner and magnet or equivalent equipment to remove stones, pieces of metal, and other non-seed objects.

The sized, cleaned, and destoned seeds are then decorticated. Decortication of sorghum seeds removes the outer husks or hulls of the seeds. Various methods of decortication may be used, such as those methods described in U.S. Pat. Nos. 5,713,526 and 5,820,039, which are each incorporated by reference in their entireties for all purposes. Other decortication methods may also be used.

After decortication, the seeds are scoured or degermed to remove the endogerm portions of the seeds. The endogerm contains fatty oils and lipids that may adversely affect the consistency and repeatability of the extrusion process. The fatty endogerm can act as a lubricant through the extrusion die, thereby degrading the extruder operation so that a consistent extruded matrix is not formed. Conventional scouring techniques may be used in removing the endogerm from the sorghum seeds. After decortication and scouring, the sorghum seeds are essentially converted into two forms of material: a by-product powder which is separated and removed and an inner-core particle for extrusion.

In order to provide an extrudable mixture from the decorticated and degermed sorghum seeds that forms the sorghum extrusion stock material, the mixture must have a certain level of moisture. A moisture level of from about $10\%_{w/w}$ to $20\%_{w/w}$ is typically required in extrudable mixtures to provide good extrusion results. In particular embodiments, a moisture level of around $16\%_{w/w}$ in the extrudable mixture has been found to be particularly useful. The desired level of moisture may be attained by the addition of water or water-containing additives to the extrudable stock material.

In some embodiments of the invention, only the sorghum extrusion stock material and any necessary water for the desired moisture content are used for the extrudable mixture in forming the extruded product. In other embodiments, however, an optional anti-fungal and/or anti-microbial agent may be added to the extrudable mixture. Such additives and their amounts are discussed and disclosed in U.S. Pat. Nos. 6,894,136; 6,939,937; and 6,965,005, each of which is incorporated herein by reference in its entirety for all purposes.

One useful naturally occurring anti-fungal/anti-microbial agent is tea tree oil or derivatives of tea tree oil. Such tea tree oil typically contains various components that include terpinen-4-ol, γ-terpinene, α-terpinene, 1-8-cieneole, para-cymene, α-pinene, α-terpineol, and α-terpinolene. The terpines of such oil are isomeric hydrocarbons that have a strong anti-fungal activity. In particular, terpinen-4-ol, γ-terpinene, α-terpinene, 1-8-cieneole, terpinolene, para-cymene, and pinene have particular uses as anti-fungal agents in the extruded products of the present invention. These individual compounds may be derived from other plant matter besides tea tree oil and may each be used in the extrudable mixture of the present invention alone or in various combinations with one another. In other embodiments, the tea tree oil itself may be used. In particular embodiments, the only additive used is tea tree oil and/or the components of tea tree oil.

Other compounds that have anti-fungal activity that may be optionally included are calcium propionate and phytoalexins, such as apigeninidin, ludeolinidin, the caffeic acid ester of arabinosyl-5-O-apigneninidin, and 5-methoxy-luteolinidin.

It may be desirable to mechanically mix the sorghum extrusion stock material and any necessary water and any optional additives in a mixing bin or container and then meter them into the extrusion equipment. Mechanical mixing helps to ensure uniform dispersion of the extrusion components.

Extrusion may be performed using various types of extrusion equipment. The incorporated references of U.S. Pat. Nos. 6,894,136; 6,939,937; and 6,965,005, disclose suitable extrusion techniques and systems that may be used in the present invention. One type of extruder that is suitable for extrusion of the sorghum mixture is a bake-type extruder or other heated extruder that elevates the extrusion temperature. Typical extrusion temperatures for sorghum extrusion are from about 325° F. to about 400° F. Associated extrusion pressures may range from about 100 psi to about 2000 psi. The particular shape and configuration of the extruder die used may be adapted to produce an extruded product matrix of a desired shape or configuration. An example of one suitable die is that having a round hole with a diameter of approximately 0.12 inches. The cutting mechanism used in the extruding equipment can be adapted to cut the extrudate into pieces having a length of from ¼ to 1½ inch, with a length of about ¾ of an inch being useful in certain applications. Other sizes and lengths may also be formed.

The extruded product may be allowed to cure after extruding. This stabilizes the product prior to storage, shipping, and use. Depending upon the matrix produced, different time periods may be required to reach equilibrium in internal moisture content.

Various densities of the extruded matrix may be desired, depending upon the application and use. In some embodiments, the extruded sorghum product may have a final density of from 0.1 lb/ft$^3$ to 0.9 lb/ft$^3$. One of the features of the present invention is that the prerequisite polyphenol level analysis of whole sorghum seeds allows the selection of sorghum extrusion stock material that provides very consistent results with density variations of the final extruded product within a very narrow range. In certain instances, variations in density may range from 0.2 lb/ft$^3$ or less.

The final extruded sorghum products may be used in a variety of applications. These include insulation materials, packing materials, pet products (toys, treats, and food), and human food/snack products.

The following examples serve to further illustrate the invention.

EXAMPLES

Example 1

The following procedures were used in evaluating relative polyphenol antioxidant levels extracted from whole sorghum seeds.

Sample Preparation

In a tared plastic weighing boat, 100.0 grams of whole sorghum seeds of different varieties to be evaluated were weighed and transferred into a 2-L Erlenmeyer flask. Solid KOH pellets were used as the polyphenol extractant base agent, with 2.00 grams being weighed into a tared plastic weighing boat and transferred to the flask. A large magnetic stirring bar was added to the flask. Finally, 400 mLs of MeOH as an extractant solvent were measured and added to the flask, and the contents were mixed.

The sample flask with the mixture was placed on hot plate with a magnetic stirrer and used with a reflux condenser with a dedicated refrigerated circulator coupled to the top of the flask. The hotplate stirring rate was set to keep the sample seeds in constant movement, and the hotplate temperature was adjusted to bring the mixture to a boil. The temperature of the refrigerated circulator was set sufficiently low to keep the solvent vapor from escaping the top of the reflux condenser. This reflux operation was continued for a period of 2 hours to complete the polyphenol extraction process.

At the end of the extraction period, the sample flask was removed from the extraction system, and the hot contents (i.e., <5° C. temperature drop) were filtered through double Whatman #1 (or equivalent) filter papers, using a vacuum filter system.

The filtrate was transferred to a 1-L round-bottom flask along with a small oval magnetic stirrer and inserted into a water bath on a hotplate stirrer. The flask was attached to an all ground-glass distillation apparatus with a dedicated refrigerated circulator. The hotplate temperature was adjusted to heat the water bath to distill off the MeOH solvent and reduce the volume of the extract sample to ~75 mLs. The distilled MeOH was saved for re-use, and the concentrated solution in the flask was transferred into a 100-mL beaker.

The beaker containing the seed extraction concentrate was placed into an icebath for 2 hours to solidify waxes and precipitate other insoluble components. The cooled concentrate was then vacuum filtered through double GF/A glass fiber filters. The filtrate was diluted with MeOH to 100 mLs to give a 1 gram seed/mL MeOH analytical sample of the sorghum variety for an HPLC analysis of polyphenol content.

HPLC Analysis

A modular HPLC system consisting of a pump, injector, column, detector, and data processing unit was employed to analyze polyphenol content in test samples. The pump of the HPLC system was a Thermo Separation Products Consta-Metric 4100 quaternary pump or equivalent programmed to deliver 2 mL of mobile phase per minute. The injector was a manual Rheodyne 7125 model equipped with a 10 µL sample loop and test samples were loaded into the injector using a Hamilton #710 100-µL HPLC syringe. The column was a Varian Microsorb-MV 250×4.6 mm C-18 reverse-phase analytical column or equivalent. The mobile phase was a binary solution of $90\%_{v/v}$ acetonitrile and $10\%_{v/v}$ 1 ppt aqueous phosphoric acid ($H_3PO_4$). The detector was a Thermo Separation Products SpectroMonitor 3200 UV/visible detector set at 323 nm. The data processing unit was a Hewlett-Packard 3396A recording integrator for recording and calculating the detected output signals.

Triplicate trials were run using a 150 ppm apigenin/luteolin standard (100 parts apigenin, 50 parts luteolin) in MeOH to determine that the HPLC system was functioning properly and to establish retention times and signal areas. Triplicate HPLC trials of the whole seed extraction samples from each sorghum variety were then run, and the results were compared to determine the presence and amounts of any polyphenol antioxidants extracted from the whole seeds. The results were reported as "ppm Polyphenol" present in the whole seed extractions.

Results

HPLC analyses showing relative polyphenol antioxidant levels extracted from whole seeds of sorghum varieties are presented in Table 1 below.

TABLE 1

| Sorghum Variety | A | B | C | D | E | F | G | H | I | J | K |
|---|---|---|---|---|---|---|---|---|---|---|---|
| ppm Polyphenol | 244 | 85 | 128 | 146 | 154 | 244 | 87 | 130 | 62 | 105 | 87 |

Example 2

Extensive extrusion tests were performed using sorghum extrusion stock materials from different varieties and mixtures of seed varieties. Some varieties were the same as those tested for relative polyphenol levels as shown in Table 1.

The results of one such set of extrusion tests are presented in Table 2 below.

TABLE 2

| Test Run | Milo Variety | ppm Polyphenols | Density (lbs/ft$^3$) | Comments on appearance and characteristics of extruded product |
|---|---|---|---|---|
| 1 | Comparative mixed | not tested | 1.03-1.13 | poor color, rough, heavy |
| 2 | Comparative B | 85 | 0.74-0.86 | rough, fair, splitting |
| 3 | Comparative G | 87 | 0.66-1.00 | rough, heavy, splitting |
| 4 | Comparative I | 62 | 0.76-1.40 | skin poor, not able to absorb $H_2O$, flaky |
| 5 | Comparative mixed | not tested | 1.04-1.13 | rough skin, poor color |
| 6 | A | 244 | 0.55-0.66 | much larger size, white color, excellent |
| 7 | D | 146 | 0.51-0.61 | low density, nice color, excellent |
| 8 | E | 154 | 0.51-0.61 | very nice, even, light, drying short |
| 9 | F | 244 | 0.54-0.57 | very nice, even, light, drying short |

Interpretation of the extrusion test results led to three conclusions. (1) Stock materials from mixed varieties of sorghum are not suitable for extrusion purposes. (2) Not all single sorghum variety stock materials yield suitable products. And (3) specific single sorghum variety stock materials from seeds having high polyphenol levels consistently yield superior products.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

I claim:

1. A method of extruding sorghum (milo) comprising:
   introducing into an extruder an extrudable mixture comprising water and a sorghum extrusion stock material consisting essentially of decorticated and degermed sorghum seeds derived from a selected single variety of sorghum seeds, the selected single variety of sorghum seeds being characterized as those sorghum seeds evaluated as intact whole seeds or whole seeds that have been converted to particles for polyphenol content to have a preselected level of polyphenols through whole sorghum seed polyphenol extraction analysis techniques; and
   operating the extruder under conditions suitable to form an extrudate product.

2. The method of claim 1, wherein:
   the preselected level of polyphenols is from 100 ppm or more.

3. The method of claim 1, wherein:
   the preselected level of polyphenols is from 150 ppm or more.

4. The method of claim 1, wherein:
   the extrudable mixture further comprises additives of calcium propionate, terpinen-4-ol, γ-terpinene, α-terpinene, 1-8-cieneole, para-cymene, α-pinene, α-terpineol, and α-terpinolene, apigeninidin, luteolinidin, the caffeic acid ester of arabinosyl-5-O-apigneninidin, and 5-methoxy-luteolinidin.

5. The method of claim 1, wherein:
   the extrudable mixture has a moisture content of from $10\%_{w/w}$ to $20\%_{w/w}$.

6. The method of claim 1, wherein:
the extrudable mixture further comprises at least one of an anti-fungal and anti-microbial agent.

7. The method of claim 1, wherein:
the extrudable mixture further comprises at least one of tea tree oil and components of tea tree oil.

8. The method of claim 1, wherein:
the extruder is operated at an extrusion temperatures of from 325° F. to 400° F.

9. The method of claim 1, wherein:
the extrusion pressure ranges from 100 psi to 2000 psi.

* * * * *

UNITED STATES PATENT AND TRADEMARK OFFICE
CERTIFICATE OF CORRECTION

PATENT NO.         : 9,702,868 B1
APPLICATION NO.    : 14/288583
DATED              : July 11, 2017
INVENTOR(S)        : Aubrie N. Starks It is certified that error appears in the above-identified patent and that said Letters Patent is hereby corrected as shown below:

In the Claims

Beginning at Column 11, Line 12 please add the following Claims 10-20:
10. The method of claim 1, wherein:
    the polyphenol extraction analysis techniques comprise:
    combining a selected amount of whole sorghum seeds to be evaluated with a solvent and a polyphenol extraction agent to form a stirrable sample mixture;
    heating the sample mixture to the approximate boiling point of the solvent with agitation of the mixture for a period of at least 1 ½ hours;
    filtering the heated mixture while the mixture is at a temperature of not more than 5 °C below the boiling point of the solvent to obtain an extractant solution filtrate that is substantially free of whole sorghum seeds;
    evaporating at least a portion of the solvent from extractant solution filtrate to form a concentrated extractant solution;
    cooling the concentrated extractant solution to facilitate solidification and/or aggregation of any fats, oils, waxes, or other materials contained within the concentrated extractant solution;
    filtering the cooled concentrated extractant solution to separate said solidified and/or aggregated fats, oils, waxes, or other materials from the cooled concentrated extractant solution to form a final filtrate;
    introducing an analytical sample of the final filtrate into a liquid chromatography system to separate polyphenol components and provide a detected output correlating to the quantity of the polyphenol components; and
    determining the relative amount of polyphenol components extracted from the whole sorghum seeds from the detected output.

11. A method of extruding sorghum (milo) comprising:
    introducing into an extruder an extrudable mixture comprising water and a sorghum extrusion stock material consisting essentially of decorticated and degermed sorghum seeds derived from a selected single variety of sorghum seeds, the selected single variety of sorghum seeds being characterized as those sorghum seeds evaluated as intact whole seeds or whole seeds that have been Signed and Sealed this
Twelfth Day of December, 2017

Joseph Matal
*Performing the Functions and Duties of the
Under Secretary of Commerce for Intellectual Property and
Director of the United States Patent and Trademark Office* converted to particles that have been converted to particles for polyphenol content to have a preselected level of polyphenols of from 100 ppm or more through whole sorghum seed polyphenol extraction analysis techniques, the polyphenol extraction analysis techniques comprising:

combining a selected amount of intact whole sorghum seeds or whole sorghum seeds that have been converted to particles to be evaluated with a solvent and a polyphenol extraction agent to form a stirrable sample mixture;

heating the sample mixture to the approximate boiling point of the solvent with agitation of the mixture for a period of at least 1 ½ hours;

filtering the heated mixture while the mixture is at a temperature of not more than 5 °C below the boiling point of the solvent to obtain an extractant solution filtrate that is substantially free of whole sorghum seeds;

evaporating at least a portion of the solvent from extractant solution filtrate to form a concentrated extractant solution;

cooling the concentrated extractant solution to facilitate solidification and/or aggregation of any fats, oils, waxes, or other materials contained within the concentrated extractant solution;

filtering the cooled concentrated extractant solution to separate said solidified and/or aggregated fats, oils, waxes, or other materials from the cooled concentrated extractant solution to form a final filtrate;

introducing an analytical sample of the final filtrate into a liquid chromatography system to separate polyphenol components and provide a detected output correlating to the quantity of the polyphenol components; and determining the relative amount of polyphenol components extracted from the whole sorghum seeds from the detected output; and operating the extruder under conditions suitable to form an extrudate product.

12. The method of claim 11, wherein:
    the preselected level of polyphenols is from 150 ppm or more.

13. The method of claim 11, wherein:
    the extrudable mixture further comprises additives of calcium propionate, terpinen-4-ol, γ-terpinene, α-terpinene, 1-8-cieneole, para-cymene, α-pinene, α-terpineol, and α-terpinolene, apigeninidin, luteolinidin, the caffeic acid ester of arabinosyl-5-O-apigneninidin, and 5-methoxy-luteolinidin.

14. The method of claim 11, wherein:
    the extrudable mixture has a moisture content of from 10 %w/w to 20 %w/w.

15. The method of claim 11, wherein:
    the extrudable mixture further comprises at least one of an anti-fungal and anti-microbial agent.

16. The method of claim 11, wherein:
    the extrudable mixture further comprises at least one of tea tree oil and components of tea tree oil.

17. The method of claim 11, wherein:
    the extruder is operated at an extrusion temperatures of from 325 °F to 400 °F.

18. The method of claim 11, wherein:
    the extrusion pressure ranges from 100 psi to 2000 psi.

19. A method of extruding sorghum (milo) comprising:
    introducing into an extruder an extrudable mixture comprising water and a sorghum extrusion stock material consisting essentially of decorticated and degermed sorghum seeds derived from a selected single variety of sorghum seeds, the extrudable mixture having a moisture content of from 10 %w/w to 20 %w/w, the selected single variety of sorghum seeds being characterized as those sorghum seeds evaluated as intact whole seeds or whole seeds that have been converted to particles for polyphenol content to have a preselected level of polyphenols of from 100 ppm or more through whole sorghum seed polyphenol extraction analysis techniques, the polyphenol extraction analysis techniques comprising:
    combining a selected amount of intact whole sorghum seeds or whole sorghum seeds that have been converted to particles to be evaluated with a solvent and a polyphenol extraction agent to form a stirrable sample mixture;
    heating the sample mixture to the approximate boiling point of the solvent with agitation of the mixture for a period of at least 1 ½ hours;
    filtering the heated mixture while the mixture is at a temperature of not more than 5 °C below the boiling point of the solvent to obtain an extractant solution filtrate that is substantially free of whole sorghum seeds;
    evaporating at least a portion of the solvent from extractant solution filtrate to form a concentrated extractant solution;
    cooling the concentrated extractant solution to facilitate solidification and/or aggregation of any fats, oils, waxes, or other materials contained within the concentrated extractant solution; filtering the cooled concentrated extractant solution to separate said solidified and/or aggregated fats, oils, waxes, or other materials from the cooled concentrated extractant solution to form a final filtrate;
    introducing an analytical sample of the final filtrate into a liquid chromatography system to separate polyphenol components and provide a detected output correlating to the quantity of the polyphenol components; and
    determining the relative amount of polyphenol components extracted from the whole sorghum seeds from the detected output; and
    operating the extruder at an extrusion temperatures of from 325 °F to 400 °F and an extrusion pressure of from 100 psi to 2000 psi to form an extrudate product.

20. The method of claim 19, wherein:
    the extrudable mixture further comprises at least one of an anti-fungal and anti-microbial agent.